United States Patent

Hoehn

[11] 3,957,782
[45] May 18, 1976

[54] PYRAZOLO [3,4-B]PYRAZINE-5-CARBOXYLIC ACIDS, ESTERS, NITRILES AND AMIDES

[75] Inventor: Hans Hoehn, Tegernheim, Germany

[73] Assignee: E. R. Squibb & Sons, Inc., Princeton, N.J.

[22] Filed: Dec. 16, 1974

[21] Appl. No.: 533,099

[52] U.S. Cl. .................... 260/250 BC; 260/243 B; 260/247.5 DP; 260/268 BC; 424/250
[51] Int. Cl.² ..................................... C07D 241/38
[58] Field of Search ............... 260/268 BC, 250 BC, 260/247.5 DP, 243 B

[56] References Cited
UNITED STATES PATENTS
3,755,340  8/1973  Hoehn et al. ............... 260/268 BC Primary Examiner—Paul M. Coughlan, Jr.
Attorney, Agent, or Firm—Lawrence S. Levinson; Merle J. Smith

[57] ABSTRACT

New derivatives of pyrazolo[3,4-b]pyrazines have the general formula:

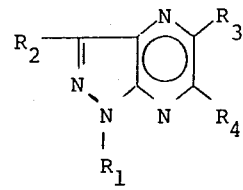

The novel compounds are useful as ataractic and antiinflammatory agents. In addition, the new compounds increase the intracellular concentration of adenosine-3',5'-cyclic monophosphate.

23 Claims, No Drawings

PYRAZOLO [3,4-b]PYRAZINE-5-CARBOXYLIC ACIDS, ESTERS, NITRILES AND AMIDES

SUMMARY OF THE INVENTION

This invention relates to a new pyrazolo[3,4-b]pyrazines and salts of these compounds. These new compounds have the formula

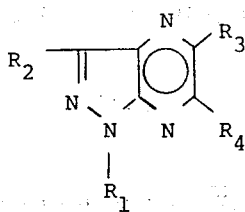

$R_1$ is hydrogen, lower alkyl, phenyl, phenyl-lower alkyl or furfuryl.

$R_2$ is hydrogen, lower alkyl or phenyl.

$R_3$ is a carboxylic acid, ester, nitrile or amide moiety. In the case of the amide, the amino group is either an acyclic group

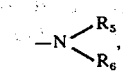

wherein $R_5$ and $R_6$ each is hydrogen, lower alkyl, phenyl or heterocyclic amino moiety wherein $R_5$ and $R_6$ together constitute a monocyclic nitrogen heterocyclic of 5 to 6 members in which an additional nitrogen, oxygen or sulfur may be present.

$R_4$ is hydroxy, lower alkoxy, lower alkylamino, lower alkyl or phenyl.

DETAILED DESCRIPTION OF THE INVENTION

A more detailed description of the groups represented by the symbols referred to above are as follows and these meanings carry throughout this specification.

The lower alkyl groups include straight or branched chain hydrocarbon groups containing 1 to 7 carbon atoms. Examples of the type of groups contemplated are methyl, ethyl, propyl, isopropyl, butyl, t-butyl, etc. The lower alkoxy and phenyl-lower alkyl groups include the preceding alkyl moieties, e.g., methoxy, ethoxy, propoxy, isopropoxy, benzyl, phenethyl and the like. Preferred are the 1 to 4 carbon alkyl groups, especially the 1 to 2 carbon members, the latter particularly in the case of the phenyl-lower alkyl groups.

The groups represented by $R_3$ more particularly are cyano or —COR substituents wherein R is hydroxy, lower alkoxy, cyanomethoxy, or

$R_5$ is hydrogen, lower alkyl or thiazole and $R_6$ is hydrogen, lower alkyl or together $R_5$ and $R_6$ complete a 5- or 6-membered nitrogen heterocyclic in which one of the additional members may be nitrogen, sulfur or oxygen, the remaining being carbon. The heterocyclics include pyrrolidine, piperidine, piperazine, (lower alkyl)piperidine, (lower alkyl)piperazino, morpholine and thiamorpholine.

Preferred embodiments of this invention are as follows:

$R_1$ and $R_2$ are hydrogen or lower alkyl, preferably hydrogen, methyl or ethyl.

$R_3$ is a carboxylic acid, ester, nitrile or amide moiety, especially —COOH, —COOethyl, —CN or mono— or disubstituted amide, i.e.,

The substituents $R_5$ and $R_6$ are hydrogen, lower alkyl, heteroyl, preferably hydrogen, butyl and thiazolyl. When joined together, $R_5$ and $R_6$ represent a monocyclic nitrogen heterocyclic, especially piperidino, piperazino or methylpiperazino.

$R_4$ is hydroxy, lower alkoxy, lower alkylamino, lower alkyl or phenyl, preferably hydroxy, ethoxy, isopentoxy, butylamino, methyl or phenyl.

The new compounds of formula I are produced by the following methods.

A 5-aminopyrazole of the formula

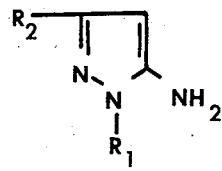

prepared according to the procedure described in Z.f Chemie 10, 386–388 (1970), is made to react with sodium nitrite (analogous to the procedure described in Gazz.) Chim. Ital. 99, 463–75 (1969) or an alkyl nitrite.

The resulting nitroso compound of the formula

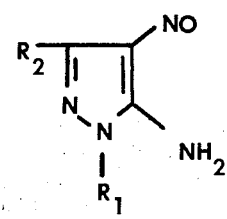

is condensed with a β-keto ester of the formula

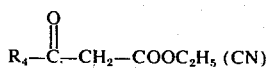 (CN)

to give a compound of the formula

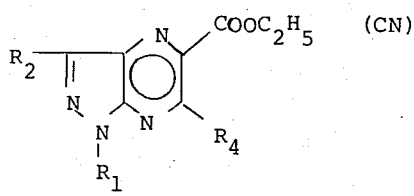 (CN)

wherein R₄ represents hydroxy, amino, lower alkyl or phenyl. As for the hydroxy and amino derivatives of formula V, both compounds are capable of existing in an equilibrium consisting of the hydroxy (amino) an oxo (imino) form of the formula

Amides of formula I are obtained by reacting the acid via the carbonyl chloride, or ester or nitrile, respectively, with an amine using known synthetic methods.

In order to prepare pyrazolo[3,4-b]pyrazines bearing a lower alkoxy or lower alkylamino group in position 6 of the molecule, a compound of the formula

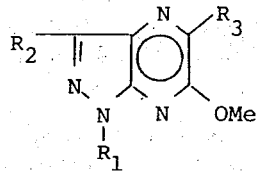

wherein R₃ is —COOH, —COOC₂H₅ or

and Me is an alkali metal or alkaline earth metal, is made to react with an alkyl halide to yield a compound of the formula

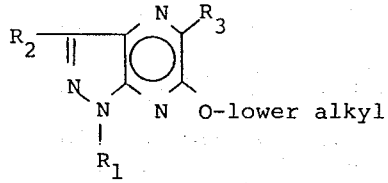

Reaction of the compound of formula Ia with an amine furnishes an amino substituted derivative of the formula

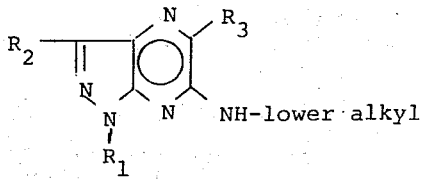

The free acids, e.g., R₃ is —COOH, are obtained from the esters by hydrolysis, for example by treatment with aqueous sodium hydroxide solution.

Compounds wherein R₁ is hydrogen are produced by an alternate process wherein R₁ is furfuryl according to the method described in U.S. Pat. No. 3,755,340, issued Aug. 28, 1973.

The compounds of this invention form various salts which are also part of this invention. For example, when $R_3$ is —COOH or $R_4$ is —OH, such compounds will form salts with metals, e.g., alkali metals such as sodium or potassium or alkaline earth metals like calcium or magnesium. When there is an amine group present, e.g., $R_4$ is lower alkylamino, such compounds will form acid addition salts with inorganic or organic acids. Such acid addition salts include the hydrohalides, like hydrochloride, hydrobromide (which are preferred), other salts of inorganic acids like sulfate, phosphate, nitrate, borate, etc. Organic acid salts include, for example, tartrate, ascorbate, acetate, citrate, succinate, methanesulfonate, toluenesulfonate, etc. Physiologically acceptable members are preferred, however, other salts frequently provide a convenient means for isolating a product, e.g., by forming and precipitating the salt in an appropriate liquid in which the salt is insoluble, then after separation of the salt, neutralizing by conventional methods to obtain the free base. Other, physiologically acceptable salts can then be formed by reaction with an equivalent proportion of the appropriate acid or base, as the case may be.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance may be utilized in compositions such as tablets, capsules, solutions or suspensions containing up to about 300 mg. per unit of dosage of a compound or mixture of compounds of formula I or physiologically acceptable salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream may also be used.

The new compounds of this invention are central nervous system depressants and can be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable salt thereof is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These are conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds also increase the intracellular concentration of adenosine-3',5'-cyclic monophosphate, and thus by the administration of about 1 to 100 mg/kg/day, preferably about 10 to 50 mg/kg, in single or two to four divided doses in conventional oral or parenteral dosage forms such as those described above may be used to alleviate the symptoms of asthma.

The following examples are illustrative of the invention. The exemplify preferred embodiments and also serve as models for the synthesis of other compounds of the invention. Appropriate choice of analogous starting materials having the desired substituent groups are merely substituted in the illustrated synthesis to obtain the other members of the series. All temperatures are in degrees celsius.

EXAMPLE 1

6-Ethoxy-1-ethyl-N-2-thiazolyl-1H-pyrazolo[3,4-b]pyrazine-5-carboxamide a. 5-Amino-1-ethyl-4-nitrosopyrazole To 111 g. of 5-amino-1-ethylpyrazole (1 mol.) dissolved in 730 ml. of ethyl acetate, 365 ml. of ethanolic hydrochloric acid (300 g. HCl/1) and 150 ml. of ethanol are added while stirring to provide a homogeneous solution. Then 117 g. of amyl nitrite (1 mol.) are added dropwise to the cooled solution (ice-sodium chloride) in order to prevent the temperature from exceeding 10°. After stirring the mixture for an additional hour, the hydrochloride of 5-amino-1-ethyl-4-nitrosopyrazole is filtered off, washed with a mixture of ethyl acetate/alcohol (3:1;) and dried, yield 125 g. (71%), m.p. 182°–184° (dec.). A sample recrystallized from a mixture of ethyl acetate alcohol (1:3) melts at 185°–186°.

Dissolving of th hydrochloride in water and neutralizing with aqueous ammonia with stirring yields the free 5-amino-1-ethyl-4-nitrosopyrazole, m.p. 135°–136° (benzene).

b. 1-Ethyl-6-hydroxy-1H-pyrazolo[3,4-b]pyrazine-5-carboxylic acid ethyl ester 94 g. of diethyl malonate (0.589 mol.) are added to a solution of 12.3 g. of sodium (0.535 mol.) in 600 ml. of abs. ethanol. After the addition of 75 g. of 5-amino-1-ethyl-4-nitrosopyrazole (0.535 mol.) to the reaction mixture, the mixture is refluxed for 4 hours with stirring. Then the alcohol is distilled off in vacuo until a thick crystal mass results. Treatment of the product with ether provides 130 g. of the sodium salt of 1-ethyl-6-hydroxy-1H-pyrazolo[3,4-b]pyrazine-5-carboxylic acid ethyl ester, hemi-hydrate, yield 88–91%.

Acidification of the sodium salt, dissolved in water by means of hydrochloric acid, yields the free ester, m.p. 138°–140° (hexane).

By substituting dimethylmalonate for the diethyl malonate, 1-ethyl-6-hydroxy-1H-pyrazolo[3,4-b]pyrazine-5-carboxylic acid methyl ester is obtained.

c. 6-Ethoxy-1-ethyl-1H-pyrazolo[3,4-b]pyrazine-5-carboxylic acid ethyl ester

A mixture of 26.7 g. of the sodium salt of 1-ethyl-6-hydroxy-1H-pyrazolo[3,4-b]pyrazine-5-carboxylic acid ethyl ester (0.1 mol.) and 31.2 g. of ethyl iodide (0.2 mol.) in 500 ml. of dimethylformamide are heated at 120°–130° in autoclave. After cooling, the solvent is removed in vacuo and the residue is stirred with 750 ml. of ether. The ethereal solution is separated from the sodium iodide and then evaporated. The oily product obtained is recrystallized from hexane to give 17.4 g. (68%) of pure 6-ethoxy-1-ethyl-1H-pyrazolo[3,4-b]pyrazine-5-carboxylic acid ethyl ester melting at 62.5°–63.5°.

By substituting 5-amino-1-methylpyrazole in the procedure of part a 6-ethoxy-1-methyl-1H-pyrazolo[3,4-b]-pyrazine-5-carboxylic acid ethyl ester is obtained.

By substituting 5-amino-1-phenylpyrazole, 5-amino-1-benzylpyrazole and 5-amino-1-phenethylpyrazole, respectively, in the procedure of part a, 6-ethoxy-1-phenyl-1H-pyrazolo[3,4-b]-pyrazine-5-carboxylic acid ethyl ester, 6-ethoxy-1-benzyl-1H-pyrazolo[3,4-b]pyrazine-5-carboxylic acid ethyl ester and 6-ethoxy-1-phenethyl-1H-pyrazolo[3,4-b]pyrazine-5-carboxylic acid ethyl ester, respectively are obtained.

d. 6-Ethoxy-1-ethyl-1H-pyrazolo[3,4-b]pyrazine-5-carboxylic acid 360 ml. of aqueous sodium hydroxide (2.5 N) are added to a solution of 47.5 g. of 6-ethoxy-1-ethyl-1H-pyrazolo[3,4-b]-pyrazine-5-carboxylic acid ethyl ester (0.18 mol.) in 360 ml. of ethanol and stirred at room temperature for 15 hours. After removing the alcohol under vacuum, the aqueous solution is acidified with concentrated hydrochloric acid to give 6-ethoxy-1-ethyl-1H-pyrazolo[3,4-b]pyrazine-5-carboxylic acid in a yield of 94%, m.p. 128°–130°. A sample recrystallized from acetonitrile melts at 130°–132°.

e. 6-Ethoxy-1-ethyl-1H-pyrazolo[3,4-b]pyrazine-5-carbonyl chloride 40 g. of 6-ethoxy-1-ethyl-1H-pyrazolo[3,4-b]pyrazine-5-carboxylic acid (0.17 mol.) and 300 ml. of thionyl chloride are refluxed for 2½ hours. After removal of the excess thionyl chloride under vacuum, the 6-ethoxy-1-ethyl-1H- pyrazolo[3,4-b]-pyrazine-5-carbonyl chloride is treated with hexane, filtered off and then dried at 60°, yield 41.5 g. (96%), m.p. 86°–87°.

f. 6-Ethoxy-1-ethyl-N-2-thiazolyl-1H-pyrazolo[3,4-b]pyrazine-5-carboxamide

A mixture of 15.3 g. of 6-ethoxy-1-ethyl-1H-pyrazolo-[3,4-b]pyrazine-5-carbonyl chloride (0.06 mol.), 6.6 g. of 2-amino-thiazole (0.66 mol.) and 9.1 ml. of triethylamine (0.66 mol.) in 400 ml. of dry benzene are refluxed for 2½ hours. After cooling the reaction mixture, the precipitated triethylamine hydrochloride is filtered off and the filtrate is evaporated to dryness. The crude 6-ethoxy-1-ethyl -N-2-thiazolyl-1H-pyrazolo-[3,4-b]pyrazine-5-carboxamide is recrystallized from ethyl acetate, m.p. 151°–152°, yield 9.9 g. (52%).

EXAMPLE 2

N-Piperidyl-6-ethoxy-1-ethyl-1H-pyrazolo[3,4-b]pyrazine-5-carboxamide 10.9 g. of 6-Ethoxy-1-ethyl-1H-pyrazolo[3,4-b]-pyrazine-5-carboxylic acid ethyl ester (0.04 mol.), prepared according to Example 1c, and 110 ml. of piperidine are heated in an autoclave at 120° for 18 hours. The clear solution is evaporated in vacuo and the residue extracted twice with 150 ml. portions of boiling hexane. The combined extracts are treated with charcoal, filtered and then evaporated to a volume of about 80 ml. The product, N-piperidyl-6-ethoxy- 1-ethyl-1H-pyrazolo[3,4-b]pyrazine-5-carboxamide, crystallizes, yield 5.7 g., m.p. 114°–115°. Recrystallization from hexane raises the melting point to 116°–117°.

EXAMPLE 3

1-Ethyl-6-hydroxy-N-2-thiazolyl-1H-pyrazolo[3,4-b]pyrazine-5-carboxamide a. 1-Ethyl-6-hydroxy-1H-pyrazolo[3,4-b]pyrazine-5-carboxylic acid 57 g. of sodium salt of 1-ethyl-6-hydroxy-1H-pyrazolo[3,4-b]pyrazine-5-carboxylic acid ethyl ester hydrate (2:1), prepared according to Example 1b, and 400 ml. of aqueous sodium hydroxide are heated to 60° with stirring for 16 hours. Then the solution is filtered and the filtrate is acidified with concentrated hydrochloric acid. The precipitated 1-ethyl-6-hydroxy-1H-pyrazolo[3,4-b]pyrazine-5-carboxylic acid is filtered off, washed with water and dried at 70°, yield 31.4 g. (71%). A sample recrystallized from acetonitrile melts at 194°–195°.

b. 1-Ethyl-6-hydroxy-1H-pyrazolo[3,4-b]pyrazine-5-carbonyl chloride 31.3 g. of 1-ethyl-6-hydroxy-1H-pyrazolo[3,4-b]-pyrazine-5-carboxylic acid (0.15 mol.) are carefully added in portions to 300 ml. of thionyl chloride. As soon as the gas evolution has ceased, the mixture is heated at reflux for 3 hours. After removal of excess thionyl chloride under vacuum, the residue is dissolved in benzene. Evaporation of the benzene provides 30.5 g. (90%) of amorphous 1-ethyl-6-hydroxy-1H-pyrazolo[3,4-b]pyrazine-5-carbonyl chloride which is used without further purification.

c. 1-Ethyl-6-hydroxy-N-2-thiazolyl-1H-pyrazolo[3,4-b]-pyrazine-5-carboxamide.

A solution of 9.2 g. of 2-aminothiazole (0.092 mol.) in 250 ml. of dry benzene is carefully added to a mixture of 21 g. of 1-ethyl-6-hydroxy-1H-pyrazolo[3,4-b]pyrazine-5-carbonyl chloride (0.92 mol.), 12.8 ml. of triethylamine (0.092 mol.) and 200 ml. of dry benzene. This is stirred at room temperature for two hours and then allowed to stand overnight. The precipitated product is filtered off and washed with water in order to remove triethylamine hydrochloride. Drying at 70°–80° yields 11.4 g. of 1-ethyl-6-hydroxy-N-2-thiazolyl-1H-pyrazolo[3,4-b]pyrazine-5-carboxamide, m.p. 252°–254° (dec.). Vacuum removal of the benzene filtrate supplies a further crop of 4 g., total yield 15.4 g. (58%). Recrystallization from glacial acetic acid raises the m.p. to 260°–261° (dec.).

EXAMPLE 4

N-Butyl-6-butylamino-1-ethyl-1H-pyrazolo[3,4-b]pyrazine-5-carboxamide 26.4 g. of 6-ethoxy-1-ethyl-1H-pyrazolo[3,4-b]-pyrazine-5-carboxylic acid ethyl ester (0.1 mol.) are heated with 190 ml. of butylamine in an autoclave at about 160° for 7 hours. After removal of the excess butylamine under vacuum, the residue is dissolved in boiling ligroin. Crystallization yields 3 g. of N-butyl-6-butylamino-1-ethyl-1H-pyrazolo[3,4-b]-pyrazine-5-carboxamide, hydrate (2:1), m.p. 128°–129° (acetonitrile). Evaporation of the ligroin filtrate supplies 27.5 g. of the hydrate free amide, m.p. 56° (ligroin), total yield 30.5 g. (95%). Treatment of the amide with ethanolic HCl yields the hydrochloride salt.

By substituting an equivalent amount of 6-ethoxy-1-methyl-1H-pyrazolo[3,4-b]pyrazine-5-carboxylic acid ethyl ester and 6-ethoxy-1-phenyl-1H-pyrazolo[3,4-b]pyrazine-5-carboxylic acid ethyl ester, respectively, as starting material, there is obtained N-butyl-6-butylamino-1-methyl-1H-pyrazolo[3,4-b]pyrazine-5-carboxamide and N-butyl-6-butylamino-1-phenyl-1H-pyrazolo-[3,4-b]pyrazine carboxamide, respectively.

EXAMPLE 5

6-Butylamino-1-ethyl-1H-pyrazolo[3,4-b]pyrazine-5-carboxylic acid and ethyl ester 23.5 g. of N-butyl-6-butylamino-1-ethyl-1H-pyrazolo-[3,4-b]pyrazine-5-carboxamide (0.0735 mol.) suspended in 230 ml. of sodium hydroxide (2.5 N) and 460 ml. of ethanol are heated at reflux for 48 hours. Then the solution is evaporated to a volume of about 60–80 ml. The sodium salt of the acid precipitates. Acidification of the pulp with dilute hydrochloric acid with stirring provides 6-butylamino-1-ethyl-1H-pyrazolo[3,4-b]pyrazine-5-carboxylic acid which is filtered off, washed with water and dried at 75°, yield 17.7 g. (91%), m.p., 97°–98° (hexane). The ester is prepared by reacting the foregoing acid with alcoholic hydrochloric acid at room temperature for 4 days. After this period, the ethanol is evaporated, the residue treated with dilute ammonia in order to remove unreacted acid and then dried at 40°. Recrystallization from ligroin yields 6-butylamino-1-ethyl-1H-pyrazolo[3,4-b]-pyrazine-5-carboxylic acid ethyl ester, m.p. 64.5°–65.5°.

EXAMPLE 6

N-Butyl-6-ethoxy-1-ethyl-1H-pyrazolo[3,4-b]pyrazine-5-carboxamide 18 g. of 6-ethoxy-1-ethyl- 1H-pyrazolo[3,4-b]pyrazine-5-carboxylic acid ethyl ester (0.068 mol.), prepared according to Example 1c, are heated with 180 ml. of butylamine in an autoclave at 70° for 5 hours. After vacuum removal of excess butylamine, the residual N-butyl-6-ethoxy-1-ethyl-1H-pyrazolo-[3,4-b]pyrazine-5-carboxamide is recrystallized from acetonitrile, m.p. 115°–117°. The mother liquor contains N-butyl-6-butyl-amino-1-ethyl-1H-pyrazolo[3,4-b]pyrazine-5-carboxamide (m.p. 128°–129°) which is identical with the compound of Example 4.

EXAMPLE 7

N-Butyl-6-ethoxy-1-ethyl-3-methyl-1H-pyrazolo[3,4-b]pyrazine-5-carboxamide a. 1-Ethyl-6-hydroxy-3-methyl-1H-pyrazolo[3,4-b]pyrazine-5-carboxylic acid ester Treatment of 5-amino-1-ethyl-3-methyl-4-nitrosopyrazole (m.p. 135°–136°), prepared according to the procedure of Example 1a, with diethylmalonate according to the procedure of Example 1b yields the sodium salt of 1-ethyl-6-hydroxy-3-methyl-1H-pyrazolo[3,4-b]pyrazine-5-carboxylic acid ethyl ester, yield 80%, m.p. 272°–273°. Neutralization provides the free ester, m.p. 160°–161° (hexane).

b. 6-Ethoxy-1-ethyl-3-methyl-1H-pyrazolo[3,4-b]pyrazine-5-carboxylic acid ethyl ester By reacting the product of Example 7a with ethyl iodide according to the procedure of Example 1c, 6-ethoxy-1-ethyl-3-methyl-1H-pyrazolo[3,4-b]pyrazine-5-carboxylic acid ethyl ester is obtained, yield 96%, m.p. 81°–82° (hexane).

c. N-Butyl-6-ethoxy-1-ethyl-3-methyl-1H-pyrazolo[3,4-b]-pyrazine-5-carboxamide 7.6 g. of 6-ethoxy-1-ethyl-3-methyl-1H-pyrazolo-[3,4-b]pyrazine-5-carboxylic acid ethyl ester (0.27 mol.) and 76 ml. of butylamine are refluxed for 1½ hours. After vacuum removal of excess butylamine, the residual N-butyl-6-ethoxy-1-ethyl-3-methyl-1H-pyrazolo[3,4-b]pyrazine-5-carboxamide is treated with ether, filtered off and dried at 70°, yield 7.2 g. (86.5%), m.p. 127°–128°.

By substituting 5-amino-1-methyl-3-phenylpyrazole for the 5-amino-1-ethylpyrazole in part a of Example 1 and proceeding as in part b of Example 1, then as in parts b and c above, 6-ethoxy-1-methyl-3-phenyl-1H-pyrazolo[3,4-b]pyrazine-5-carboxylic acid ethyl ester and N-butyl-6-ethoxy-1-methyl-3-phenyl-1H-pyrazolo-[3,4-b]pyrazine-5-carboxamide are obtained.

EXAMPLE 8

6-Ethoxy-1-ethyl-3-methyl-N-2-thiazolyl-1H-pyrazolo[3,4-b]-pyrazine-5-carboxamide a. 6-Ethoxy-1-ethyl-3-methyl-1H-pyrazolo[3,4-b]pyrazine-5-carboxylic acid 2.78 g. of 6-ethoxy-1-ethyl-3-methyl-1H-pyrazolo-[3,4-b]pyrazine-5-carboxylic acid ethyl ester (0.01 mol.) dissolved in 20 ml. of ethanol are added to 20 ml. of aqueous sodium hydroxide (2.5 N) and the solution is allowed to stand overnight. After the vacuum removal of the alcohol, the solution is acidified with concentrated hydrochloric acid, the precipitated 6-ethoxy-1-ethyl-3methyl-1H-pyrazolo[3,4-b]pyrazine-5-carboxylic acid is filtered off, washed with water and dried at 70°, yield 2 g. (80%), m.p. 172°.

b. 6-Ethoxy-1-ethyl-3-methyl-1H-pyrazolo[3,4-b]pyrazine-5-carbonyl chloride 22.7 g. of 6-ethoxy-1-ethyl-3-methyl-1H-pyrazolo-[3,4-b]pyrazine-5-carboxylic acid (0.09 mol.) and 250 ml. of thionyl chloride are heated at reflux temperature for two hours. After vacuum removal of excess thionyl chloride, the residual 6-ethoxy-1-ethyl-3-methyl-1H-pyrazolo[3,4-b]pyrazine-5-carbonyl chloride is recrystallized from hexane, yield 20.5 g. (85%), m.p. 109°–111°.

c. 6-Ethoxy-1-ethyl-3-methyl-N-2-thiazolyl-1H-pyrazolo-[3,4-b]pyrazine-5-carboxamide 15.75 g. of 6-ethoxy-1-ethyl-3-methyl-1H-pyrazolo[3,4-b]-pyrazine-5-carbonyl chloride (0.058 mol.) are dissolved in 150 ml. of dry toluene. To this well cooled solution (ice/sodium chloride) a solution of 6.4 g. of 2-aminothiazole (0.638 mol.) and 6.5 g. of triethylamine (0.638 mol.) in 260 ml. of dry toluene is added dropwise under stirring. The reaction temperature is kept at −5° to −10°. Then stirring is continued at room temperature for 1 hour and at 50° for 1 hour. The precipitated triethylamine hydrochloride is filtered off and the toluene filtrate is removed in vacuo. Recrystallization of the residual 6-ethoxy-1-ethyl-3-methyl-N-2-thiazolyl-1H-pyrazolo[3,4-b]pyrazine-5-carboxamide gives 15.4 g. of product (78%), m.p. 158°–159°.

EXAMPLE 9

(6-Ethoxy-1-ethyl-3-methyl-1H-pyrazolo[3,4-b]pyrazin-5-yl) (4-methyl-1-piperazinyl)methanone By substituting an equivalent amount of 4-methylpiperazine for the 2-aminothiazole in the procedure of Example 8c, (6-ethoxy-1-ethyl-3-methyl-1H-pyrazolo[3,4-b]-pyrazin-5-yl) (4-methyl-1-piperazinyl)methanone is obtained, yield 84%, m.p. 111°–112° (hexane).

EXAMPLE 10

6-Ethoxy-1-ethyl-1H-pyrazolo[3,4-b]pyrazine-5-carbonitrile a. 1-Ethyl-6-hydroxy-1H-pyrazolo[3,4-b]pyrazine-5-carbo-nitrile and 1-ethyl-6-amino-1H-pyrazolo[3,4-b]pyrazine-5-carboxylic acid ethyl ester To a solution of 8.05 g. of sodium (0.35 mol.) in 400 ml. of absolute ethanol, 43.5 g. of cyanoacetic acid ethyl ester (0.385 mol.) is added and the mixture is stirred for 30 minutes. After adding 49 g. of 5-amino-1-ethyl-4-nitrosopyrazole (0.35 mol.), the mixture is heated at reflux for 4 hours. Then, the precipitate, consisting of the nitrile and the ester, is filtered off and dried at 60° yielding 43.2 g. of material. By treatment with water the nitrile dissolves as the sodium salt. The undissolved 1-ethyl-6-amino-1H-pyrazolo[3,4-b]pyrazine-5-carboxylic acid ethyl ester is recrystallized from acetonitrile, yield 6.7 g. (10.2%), m.p. 188°–189°.

The aqueous filtrate is acidified with concentrated hydrochloric acid, the precipitate is filtered off and dried at 70°. Recrystallization from acetonitrile yields 19 g. of 1-ethyl-6-hydroxy-1H-pyrazolo[3,4-b]pyrazine-5-carbonitrile, m.p. 232°–233° (dec.). An additional crop of 9.1 g. is obtained by vacuum removal of the alcoholic mother liquor, dissolving the residual sodium salt in water and acidifying with concentrated hydrochloric acid, total yield 28.1 g. (42.5%).

b. 6-Ethoxy-1-ethyl-1H-pyrazolo[3,4-b]pyrazine-5-carbonitrile 18.9 g. of 1-ethyl-6-hydroxy-1H-pyrazolo[3,4-b]-pyrazine-5-carbonitrile (0.1 mol.) are added to a solution of 2.3 g. of sodium (0.1 mol.) in 500 ml. of absolute ethanol and the mixture is stirred for 30 minutes at room temperature. Then the alcohol is distilled off in vacuo and the sodium salt is dissolved in dry dimethylformamide. Then 23.5 g. of ethyl iodide (0.15 mol.) are added and the solution is heated in an autoclave at 120° for 5 hours. After the dimethylformamide is removed in vacuo, the residual 6-ethoxy-1-ethyl-1H-pyrazolo[3,4-b]pyrazine-5-carbonitrile (19.1 g.) is recrystallized from hexane, yield 17 g. (78%), m.p. 73°–74°.

EXAMPLE 11

1-Ethyl-6-isopentyloxy-1H-pyrazolo[3,4-b]pyrazine-5-carbonitrile

By substituting an equivalent amount of isopentyl bromide for the ethyl iodide in the procedure of Example 10b, 1-ethyl-6-isopentyloxy-1H-pyrazolo[3,4-b]-pyrazine-5-carbo-nitrile is obtained, yield 75%, m.p. 78°–80° (hexane).

EXAMPLE 12

1-Ethyl-6-isopentyloxy-3-methyl-1H-pyrazolo[3,4-b]pyrazine-5-carboxylic acid ethyl ester 4.89 g. of potassium carbonate (0.035 mol.) are added to a solution of 7.36 g. of 1-ethyl-6-hydroxy-3-methyl-1H-pyrazolo[3,4-b]carboxylic acid ethyl ester (0.029 mol.) dissolved in 110 ml. of dry dimethylformamide and is stirred at room temperature for 30 minutes. Then 8.88 g. of isopentyl bromide (0.058 mol.) are added and stirring is continued at 60° for 2 hours. After vacuum removal of the dimethylformamide, the residue is treated with ether, potassium bromide is filtered off and the ethereal filtrate evaporated. Recrystallization of the residual 1-ethyl-6-isopentyloxy-3-methyl-1H-pyrazolo-[3,4-b]pyrazine-5-carboxylic acid ethyl ester from hexane yields 9 g. (95.8%) of material, m.p. 59°–61°.

EXAMPLE 13

1-Ethyl-6-phenyl-1H-pyrazolo[3,4-b]pyrazine-5-carboxylic acid and ethyl ester 288 g. of benzoylacetic acid ethyl ester (1.5 mol.) are added to a solution of 34.5 g. of sodium (1.5 mol.) in 2.1 l. of absolute ethanol and stirred at room temperature for 30 minutes. Then 210 g. of 5-amino-1-ethyl-4-nitrosopyrazole (1.5 mol.) are added and stirring of the mixture is continued at reflux temperature for 2½ hours. After cooling, the precipitated compound is filtered off and washed with ethanol and treated with water. The undissolved material consists of 1-ethyl-6-phenyl-1H-pyrazolo[3,4-b]pyrazine-5-carboxylic acid ethyl ester (10 g.), m.p. 73°–74° (hexane), whereas the aqueous filtrate, after acidification with dilute hydrochloric acid yields 111 g. of 1-ethyl-6-phenyl-1H-pyrazolo[3,4-b]pyrazine-5-carboxylic acid. The crude acid melts at 154°–155° (dec.). When recrystallized from acetonitrile, it melts at 158°–159° (dec.).

Evaporation of the alcoholic mother liquor and work up in the foregoing manner gives an additional crop of 65 g. of ester and 63 g. of crude acid. The latter is treated with hexane in order to remove 5-benzoyl-1-ethyl-6-hydroxy-1H-pyrazolo[3,4-b]pyrazine (14 g.) as the by-product. The total yield of the acid amounts to 160 g. (40%) and of the ester 75 g. (17%).

EXAMPLE 14

N-Butyl-1-ethyl-6-phenyl-1H-pyrazolo[3,4-b]pyrazine-5-carboxamide 3.7 g. of 1-ethyl-6-phenyl-1H-pyrazolo[3,4b]pyrazine-5-carboxylic acid ethyl ester (0.0125 mol.) and 37 ml. of butylamine are heated in an autoclave at 120° for 15 hours. After vacuum removal of the excess butylamine, the residual N-butyl-1-ethyl-6-phenyl-1H-pyrazolo[3,4-b]pyrazine-5-carboxamide is recrystallized from acetonitrile, yield 3.95 g. (97%), m.p. 127°–128°.

EXAMPLE 15

1-Ethyl-6-phenyl-1H-pyrazolo[3,4-b]pyrazine-5-carboxylic acid, cyanomethyl ester 5.8 g. of the sodium salt of 1-ethyl-6-phenyl-1H-pyrazolo[3,4-b]pyrazine-5-carboxylic acid (0.02 mol.), 1.7 g. of chloroacetonitrile (0.22 mol.) and 70 ml. of dry dimethyl-formamide are heated in an autoclave at 120° for 5 hours. After vacuum removal of the solvent, the residual 1-ethyl-6-phenyl-1H-pyrazolo[3,4-b]pyrazine-5-carboxylic acid, cyano-methyl ester is treated with water, filtered off, again treated with alcohol and then recrystallized from ethanol, yield 3.9 g. (64%), m.p. 102°–103°.

EXAMPLE 16

1-Ethyl-6-phenyl-1H-pyrazolo[3,4-b]pyrazine-5-carboxamide 8.4 g. of 1-ethyl-6-phenyl-1H-pyrazolo[3,4-b]pyrazine-5-carboxylic acid ethyl ester (0.028 mol.) and 50 ml. of alcoholic ammonia (85 g. NH$_3$/1) are heated in an autoclave at 200° for 5½ hours and the product is worked up according to the procedure of Example 14. The residual 1-ethyl-6-phenyl-1H-pyrazolo[3,4- b]pyrazine-5-carboxamide is treated with hexane and then recrystallized from ethyl acetate, yield 2.7 g. (37%), m.p. 189°–190°.

EXAMPLE 17

1-Ethyl-N-methyl-6-phenyl-1H-pyrazolo[3,4-b]pyrazine-5-carboxamide

By substituting an equivalent amount of methylamine for ammonia in the procedure of Example 16, 1-ethyl-N-methyl-6-phenyl-1H-pyrazolo[3,4-b]pyrazine-5-carboxamide is obtained, yield 85%, m.p. 165°–166° (hexane/ethanol)

EXAMPLE 18

1-Ethyl-6-phenyl-N-2-thiazolyl-1H-pyrazolo[3,4-b]pyrazine-5-carboxamide

Conversion of 6-ethoxy-1-ethyl-1H-pyrazolo[3,4-b]-pyrazine-5-carboxylic acid to the corresponding carbonyl chloride, by the procedure of Example 1e, and reaction with 2-amino-thiazole according to the procedure of Example 1f, yields 1-ethyl-6-phenyl-N-2-thiazolyl-1H-pyrazolo[3,4-b]pyrazine-5-carboxamide, yield 57%, m.p. 194°–196° (ethanol).

EXAMPLES 19 – 21

The following additional compounds are prepared by the procedure of Example 18:

1-Ethyl-N-(1-methylpropyl)-6-phenyl-1H-pyrazolo-[3,4-b]pyrazine-5-carboxamide, yield 70%, m.p. 150°–151° (hexane/ethanol, 2:1).

N,N,1-Triethyl-6-phenyl-1H-pyrazolo[3,4-b]pyrazine-5-carboxamide, yield 64%, m.p. 111°–112° (hexane).

(1-Ethyl-6-phenyl-1H-pyrazolo[3,4-b]pyrazine-5-yl)(4-methyl-1-piperazinyl)methanone, yield 89%, m.p. 170°–171° (ethanol).

EXAMPLE 22

N-Butyl-1-ethyl-6-methyl-1H-pyrazolo[3,4-b]pyrazine-5-carboxamide a. 1-Ethyl-6-methyl-1H-pyrazolo[3,4-b]pyrazine-5-carboxylic acid 49 g. of 5-amino-1-ethyl-4-nitrosopyrazole (0.35 mol.) are added to a solution of 8.05 g. of sodium (0.35 mol.) in 350 ml. of absolute ethanol and this is stirred at room temperature for 30 minutes. After the addition of 50 g. of acetoacetic acid ethyl ester (0.385 mol.) the reaction mixture is heated at reflux temperature for 3½ hours. The precipitated sodium salt is filtered off, washed with ether and dried at 50°, yield 47.1 g. (59%). By dissolving the sodium salt in water, treatment with charcoal and acidification with concentrated hydrochloric acid, 1-ethyl-6-methyl-1H-pyrazolo-[3,4-b]pyrazine-5-carboxylic acid, m.p. 148°–149° (ethanol) is obtained.

b. 1-Ethyl-6-methyl-1H-pyrazolo[3,4-b]pyrazine-5-carboxylic acid, ethyl ester 12.1 g. of 1-ethyl-6-methyl-1H-pyrazolo[3,4-b]pyrazine-5-carboxylic acid (0.059 mol.) are added to a solution of 1.36 of sodium (0.059 mol.) in 250 ml. of absolute ethanol and is stirred for 30 minutes at room temperature. The alcohol is distilled off in vacuo and the sodium salt is dissolved in 350 ml. of dry dimethylformamide. Then, 14 g. of ethyl iodide (0.88 mol.) are added and the solution is heated in an autoclave at 120° for 10 hours. After the dimethylformamide has been removed in vacuo, the residual 1-ethyl-6-methyl-1H-pyrazolo[3,4-b]pyrazine-5-carboxylic acid ethyl ester is treated with water, dried at 50° and recrystallized from hexane, yield 9.4 g. (68%), m.p. 64°–65°.

c. N-Butyl-1-ethyl-6-methyl-1H-pyrazolo[3,4-b]pyrazine-5-carboxamide

By substituting an equivalent amount of 1-ethyl-6-methyl-1H-pyrazolo[3,4-b]pyrazine-5-carboxylic acid ethyl ester for 1-ethyl-6-phenyl-1H-pyrazolo[3,4-b]pyrazine-5-carboxylic acid ether ester in the procedure of Example 14, N-butyl-1-ethyl-6-methyl-1H-pyrazolo[3,4-b]pyrazine-5-carboxamide is obtained, yield 48%, m.p. 64°–65° (hexane).

EXAMPLE 23

1-Ethyl-6-methyl-1H-pyrazolo[3,4-b]pyrazine-5-carboxylic acid, cyanomethyl ester 9.12 g. of the sodium salt of 1-ethyl-6-methyl-1H-pyrazolo[3,4-b]pyrazine-5-carboxylic acid (0.04 mol.), 3.33 g. of chloroacetonitrile (0.056 mol.) and 90 ml. of dimethyl-formamide are stirred at 70°–80° for 12 hours. After vacuum removal of the dimethylformamide, the residue is stirred with 200 ml. of ether and filtered. The ethereal filtrate is evaporated and the residual 1-ethyl-6-methyl-1H-pyrazolo[3,4-b]-pyrazine-5-carboxylic acid, cyanomethyl ester is recrystallized from hexane, yield 3.76 g. (38%), m.p. 83°–84°. A polymorphous form melts at 111°–112°.

EXAMPLE 24

N-Butyl-6-butylamino-1H-pyrazolo[3,4-b]pyrazine-5-carboxamide

By substituting 1-(2-furyl)methyl-5-aminopyrazole for the 5-amino-1-ethylpyrazole in the procedure of Example 1a and following the procedure of parts b and c, 6-ethoxy-1-(2-furyl)-methyl-1H-pyrazolo[3,4-b]pyrazine-5-carboxylic acid ethyl ester is obtained. This product is treated with an excess of selenium dioxide according to the procedure of Example 56 in U.S. Pat. No. 3,755,340, issued Aug. 28, 1973, to obtain 6-ethoxy-1H-pyrazolo[3,4-b]pyrazine-5-carboxylic acid ethyl ester. Reaction of this product with butylamine as in Example 4 yields N-butyl-6-butylamino-1H-pyrazolo[3,4-b]pyrazine carboxamide.

What is claimed is:

1. A compound of the formula

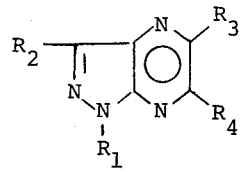

wherein
  R₁ is hydrogen, lower alkyl, phenyl, phenyl-lower alkyl or furfuryl;
  R₂ is hydrogen, lower alkyl or phenyl;
  R₃ is cyano or —COR wherein R is hydroxy, lower alkoxy, cyanomethoxy or

R₄ is hydroxy, lower alkoxy, lower alkylamino, lower alkyl or phenyl;

R₅ is hydrogen, lower alkyl or thiazole;

R₆ is hydrogen or lower alkyl; or R₅ and R₆ together with the nitrogen are pyrrolidino, piperidino, piperazino, (lower alkyl)piperidino, (lower alkyl)-piperazino, morpholino or thiamorpholino;

said lower alkyl groups having up to seven carbon atoms, and salts thereof.

2. A compound as in claim 1 wherein R₁ and R₂ each is hydrogen or lower alkyl; R₃ is cyano or —COR wherein R is hydroxy, lower alkoxy or

wherein R₅ is hydrogen, lower alkyl or thiazolyl and R₆ is hydrogen or lower alkyl or N, R₅ and R₆ together are piperidino, piperazino or (lower alkyl)-piperazino; and R₄ is hydroxy, lower alkoxy, lower alkylamino, lower alkyl or phenyl.

3. A compound as in claim 1 wherein R₃ is —COR and R is hydroxy or lower alkoxy.

4. A compound as in claim 1 wherein R₃ is cyano.

5. A compound as in claim 1 wherein R₃ is —COR and R is lower alkylamino.

6. A compound as in claim 1 wherein R₃ is —COR and R is piperidino.

7. A compound as in claim 1 wherein R₃ is —COR and R is (2-thiazolyl)amino.

8. A compound as in claim 1 wherein R₃ is —COR and R is (lower alkyl)piperazino.

9. A compound as in claim 1 wherein R₃ is —COR and R is di(lower alkyl)amino.

10. A compound as in claim 1 wherein R₃ is —COR and R is cyanomethoxy.

11. A compound as in claim 1 wherein R₄ is hydroxy.

12. A compound as in claim 1 wherein R₄ is lower alkoxy.

13. A compound as in claim 1 wherein R₄ is lower alkylamino.

14. A compound as in claim 1 wherein R₄ is lower alkyl.

15. A compound as in claim 1 wherein R₄ is phenyl.

16. A compound as in claim 1 wherein R₁ is lower alkyl, R₂ is hydrogen, R₃ is —COR and R is lower alkylamino, and R₄ is lower alkylamino.

17. The compound as in claim 16 wherein R₁ is ethyl, R₃ is —COR and R is butylamino, and R₄ is butylamino.

18. A compound as in claim 1 wherein R₁ is lower alkyl, R₂ is hydrogen, R₃ is cyano and R₄ is hydroxy or lower alkoxy.

19. The compound as in claim 18 wherein R₁ is ethyl and R₄ is ethoxy.

20. A compound as in claim 1 wherein R₁ is lower alkyl, R₂ is hydrogen, R₃ is —COR and R is lower alkoxy, and R₄ is hydroxy or lower alkoxy.

21. The compound as in claim 20 wherein R₁ is ethyl, R₃ is —COR and R is ethoxy, and R₄ is ethoxy.

22. A compound as in claim 1 wherein R₁ is lower alkyl, R₂ is hydrogen, R₃ is —COR and R is lower alkylamino and R₄ is phenyl.

23. The compound as in claim 22 wherein R₁ is ethyl, R₃ is —COR and R is butylamino.

* * * * *